US009539181B2

(12) United States Patent
Phillips et al.

(10) Patent No.: US 9,539,181 B2
(45) Date of Patent: Jan. 10, 2017

(54) KINK-RESISTANT TUBING

(71) Applicant: Applied Medical Technology, Inc., Brecksville, OH (US)

(72) Inventors: Grant W. Phillips, Richfield, OH (US); Derek M. Williams, Cuyahoga Falls, OH (US); George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 0 days.

(21) Appl. No.: 14/838,895

(22) Filed: Aug. 28, 2015

(65) Prior Publication Data

US 2015/0366761 A1 Dec. 24, 2015

Related U.S. Application Data

(63) Continuation of application No. 14/138,780, filed on Dec. 23, 2013, now abandoned.

(60) Provisional application No. 61/745,640, filed on Dec. 23, 2012.

(51) Int. Cl.
*A61J 15/00* (2006.01)
*A61M 25/00* (2006.01)

(52) U.S. Cl.
CPC ......... *A61J 15/0003* (2013.01); *A61J 15/0015* (2013.01); *A61J 15/0069* (2013.01); *A61J 15/0073* (2013.01); *A61M 25/005* (2013.01); *A61M 25/0009* (2013.01); *A61M 2025/0059* (2013.01)

(58) Field of Classification Search
CPC ...... A61J 15/00; A61J 15/0015; A61J 15/003; A61J 15/0069; A61J 15/0073; A61M 25/0012
See application file for complete search history.

(56) References Cited

U.S. PATENT DOCUMENTS

| 4,668,225 | A | * | 5/1987 | Russo | A61J 15/0015 604/104 |
|---|---|---|---|---|---|
| 4,698,059 | A | * | 10/1987 | Johnson | C08K 3/08 604/270 |
| 5,527,280 | A | | 6/1996 | Goelz | |
| 5,879,499 | A | | 3/1999 | Corvi | |
| 6,077,243 | A | | 6/2000 | Quinn | |
| 6,623,490 | B1 | | 9/2003 | Crane et al. | |
| 2005/0197624 | A1 | | 9/2005 | Goodson, IV et al. | |
| 2005/0222581 | A1 | | 10/2005 | Fischer, Jr. et al. | |

(Continued)

FOREIGN PATENT DOCUMENTS

| EP | 2 067 465 A2 | 6/2009 |
| SU | 927254 A1 | 5/1982 |

OTHER PUBLICATIONS

International Search Report for Application No. PCT/US13/77484; Dated Apr. 17, 2014.

*Primary Examiner* — Imani Hayman
*Assistant Examiner* — James D Ponton
(74) *Attorney, Agent, or Firm* — Pearne & Gordon LLP

(57) ABSTRACT

Tubing for use in gastrointestinal applications includes a hollow tube and a spring positioned inside the tube. The spring is corrosion resistant and helps to prevent kinking of the tubing when the tubing is bent. An encapsulant may be positioned over the spring. The spring may be co-extruded with the tubing.

11 Claims, 13 Drawing Sheets

(56) References Cited

U.S. PATENT DOCUMENTS

| | | | |
|---|---|---|---|
| 2007/0162108 A1* | 7/2007 | Carlson | A61B 17/12022 |
| | | | 623/1.34 |
| 2008/0108974 A1* | 5/2008 | Yee Roth | A61L 29/085 |
| | | | 604/529 |
| 2008/0140055 A1 | 6/2008 | Shirley | |
| 2009/0149834 A1* | 6/2009 | Moss | A61M 25/0012 |
| | | | 604/524 |
| 2009/0281500 A1 | 11/2009 | Acosta et al. | |
| 2010/0036365 A1* | 2/2010 | Becker | A61M 39/10 |
| | | | 604/533 |
| 2012/0203171 A1 | 8/2012 | Williams et al. | |
| 2014/0024955 A1 | 1/2014 | Zhadkevich | |

* cited by examiner

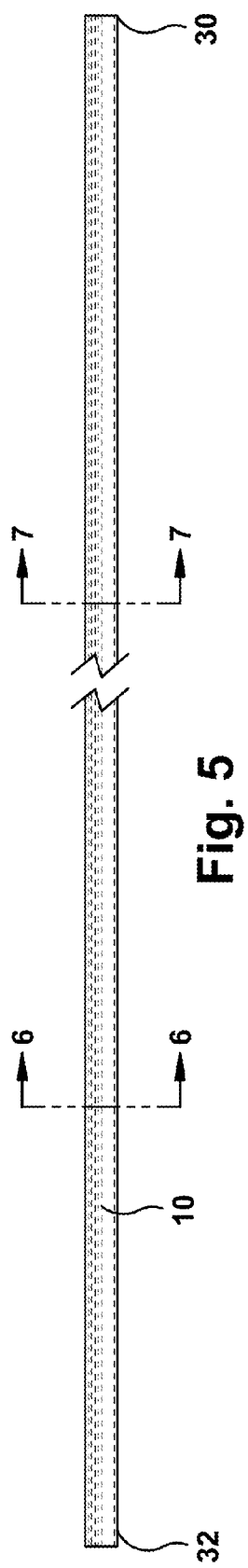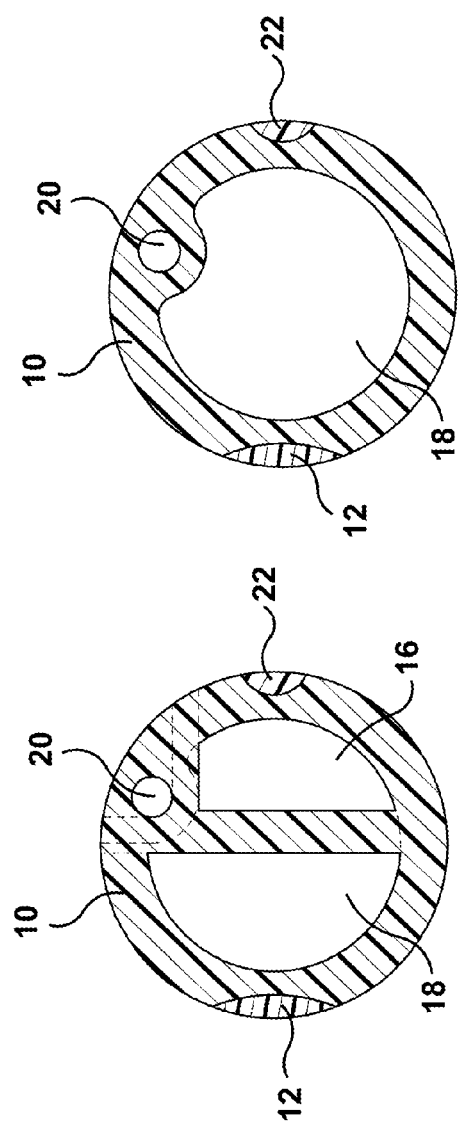

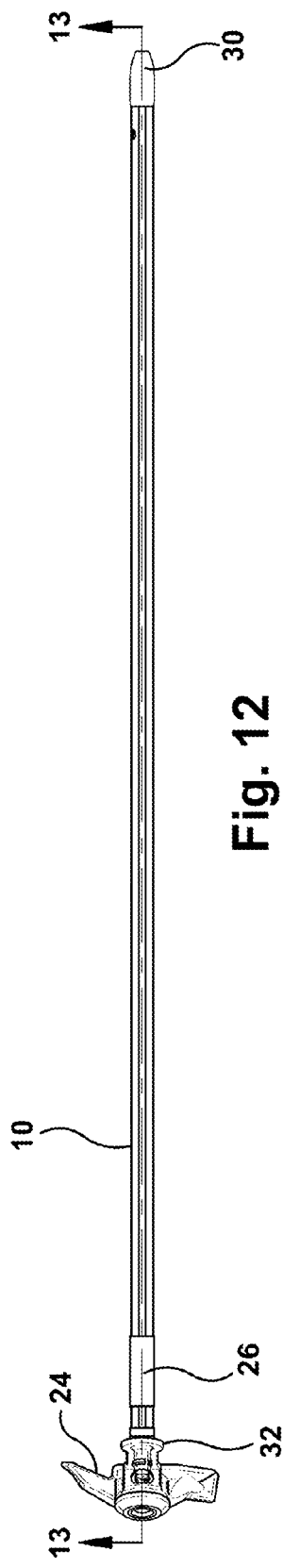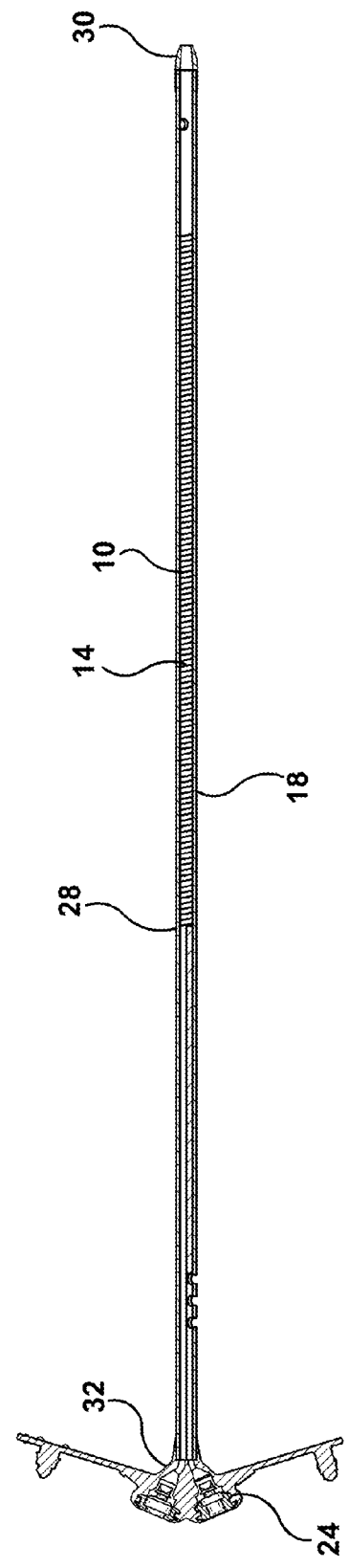
Fig. 12
Fig. 13

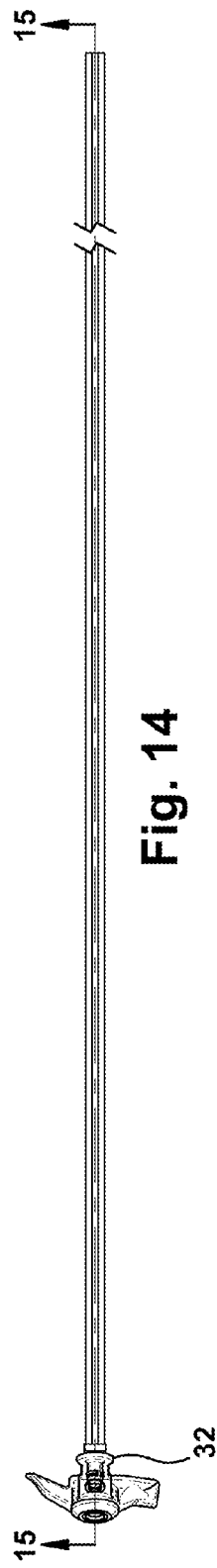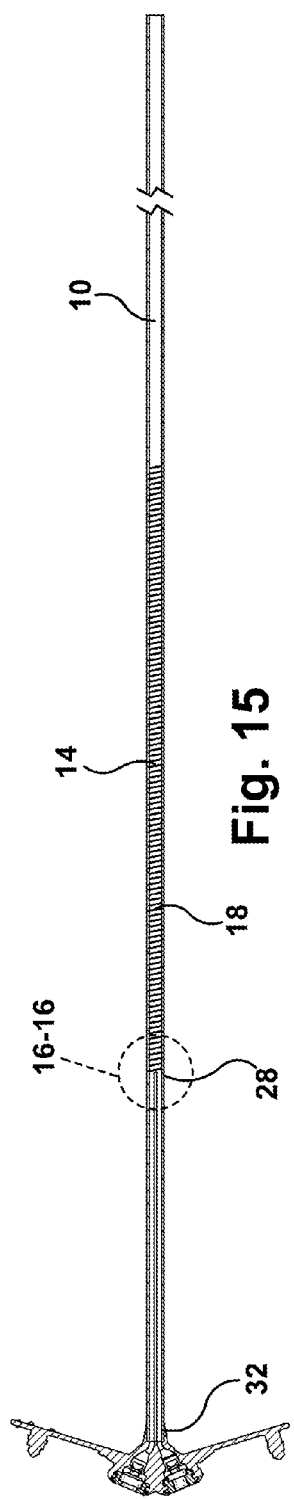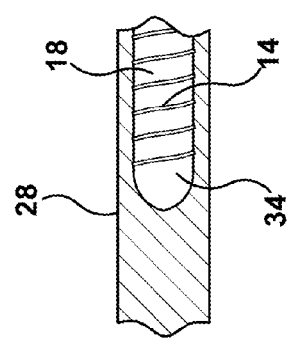

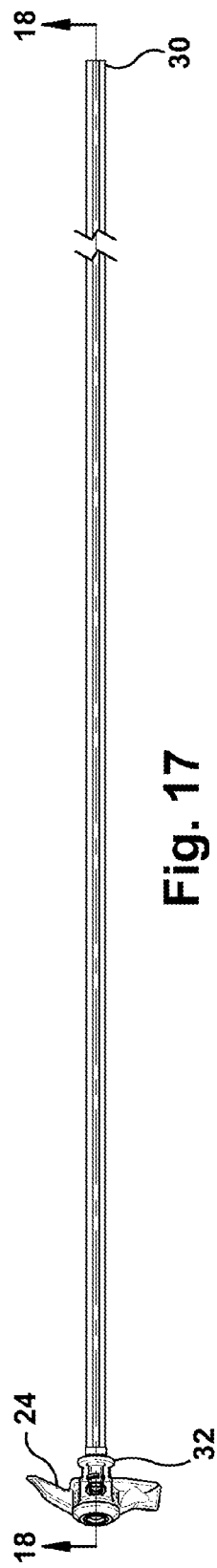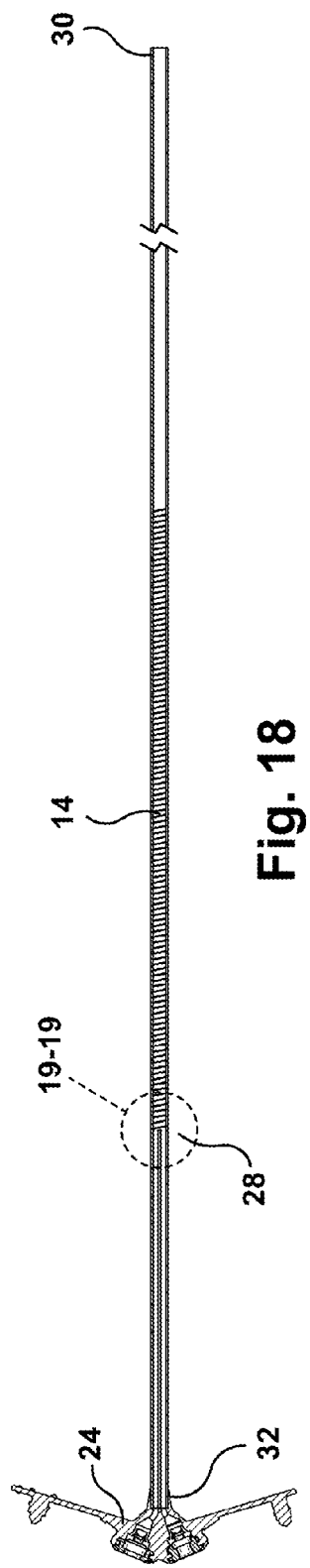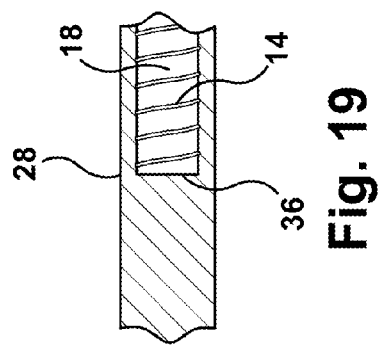

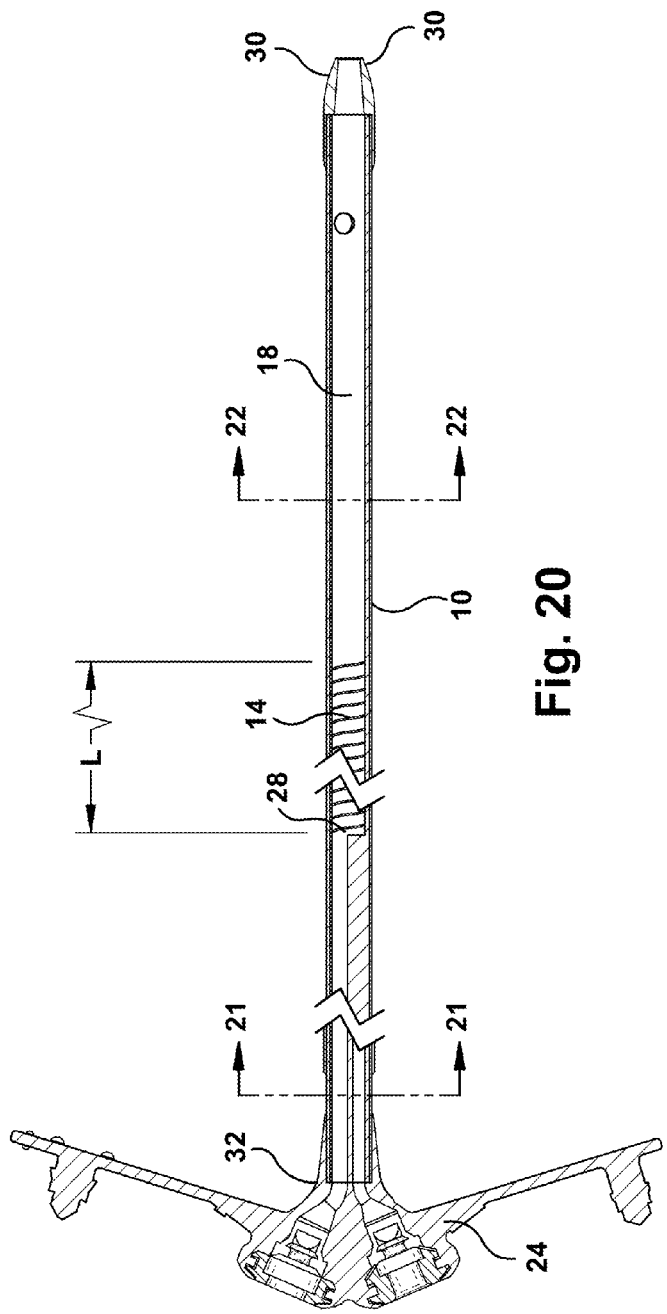
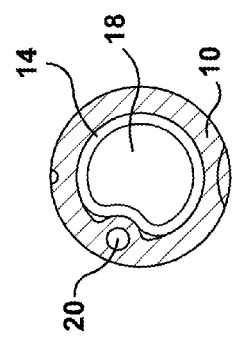
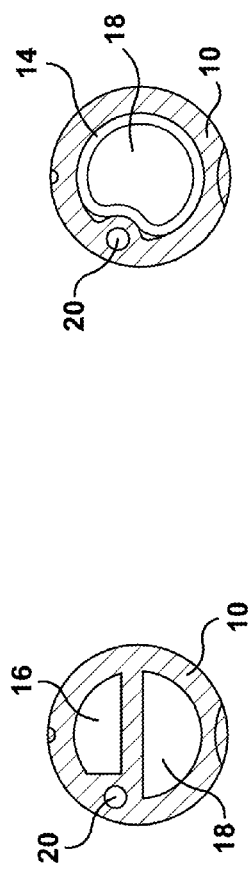
Fig. 20
Fig. 21
Fig. 22

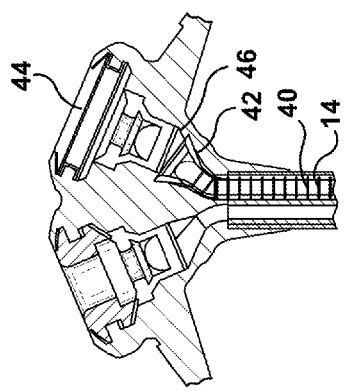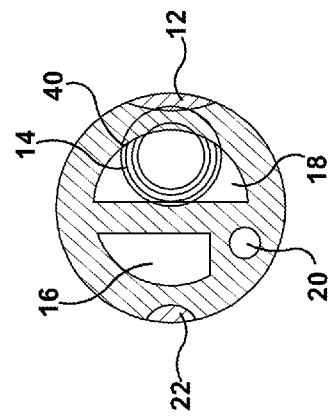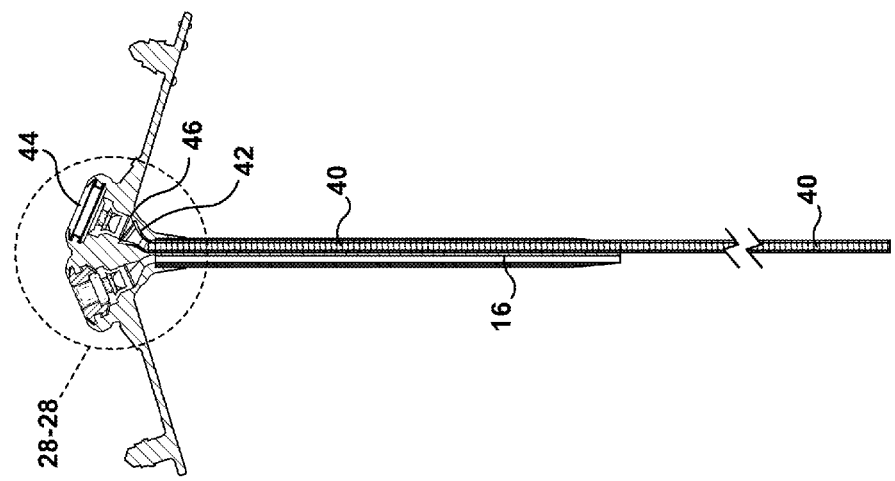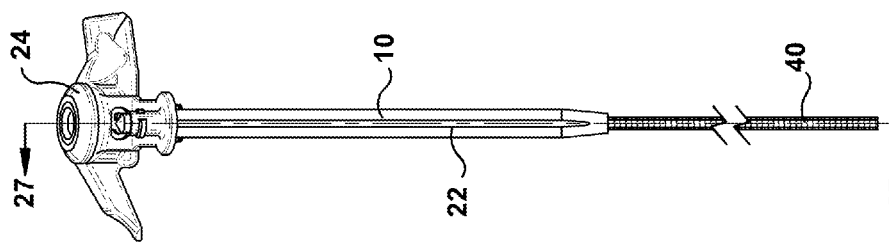

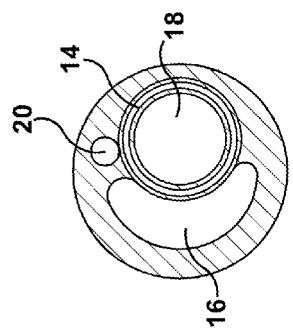
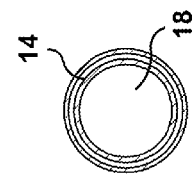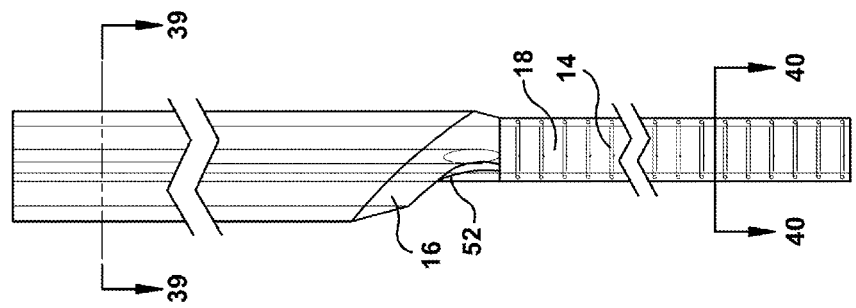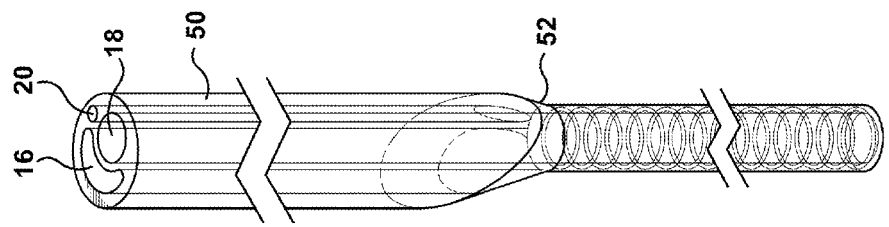

KINK-RESISTANT TUBING

CROSS-REFERENCE TO RELATED APPLICATION

This application is continuation of U.S. Non-Provisional application Ser. No. 14/138,780, filed on Dec. 23, 2013, which claims the priority of U.S. Provisional Application No. 61/745,640, filed on Dec. 23, 2012, both of which are hereby incorporated by reference.

FIELD

The examples described herein concern kink-resistant tubing. One application for the example kink-resistant tubing is in gastrointestinal applications.

BACKGROUND

Low profile gastrojejunostomy ("G-J") feeding tubes have been developed for use in smaller patients, such as pediatric patients, in small sizes such as 14 French. As the G-J feeding tubes are placed in younger and younger patients, the intestinal anatomy that the device is used in also becomes smaller. The jejunal portion of the small intestine in infants is very tight, compact and tortuous. The entire gastrointestinal tract fits in an abdominal cavity roughly the size of a softball. Each twist and turn of the jejunum must be navigated by the distal portion of the G-J device tube.

As the jejunal path becomes more tortuous, the probability of kinking of the G-J tube increases. If the tubing kinks, the device is rendered ineffective and must be replaced with a new device. Most patients that depend upon direct jejunal feedings for nutrition cannot tolerate a kinked tube for very long. Since most G-J device placements are performed by interventional radiology, the occurrence (or reoccurrence) of this expensive procedure, which is typically scheduled in advance, is something that hospitals and insurance companies would like to limit. Parents of pediatric patients would also like to reduce the time spent at the hospital, as well as the amount of radiation exposure to their children during fluoroscopy placements. Examples of kinked G-J tubing known in the prior art are shown in FIGS. 1 and 2. FIG. 1 depicts a kinked multi-lumen tube 2 and FIG. 2 depicts a kinked single lumen tube 4. As is evident, kinking involves restricting flow through the tubing either partially or entirely.

SUMMARY

A kink resistant tubing is disclosed and described herein. In one example, tubing for use in gastrointestinal applications includes a hollow tube and a spring coupled to the tube. The spring is corrosion resistant and helps to prevent kinking of the tubing when the tubing is bent. The spring may be positioned against an inner diameter of the hollow tube and may also include an encapsulant positioned over the tubing. The spring may be made of a stainless steel or a polymeric material. The tubing may be made of a silicone material, a polyurethane material, or a polymeric material. The tubing may have a substantially round inner diameter, or the tubing may not have a substantially round interior surface. The spring may be positioned in the hollow tube during a tube extrusion manufacturing process such that the spring is embedded in a wall of the tubing, or the spring may be positioned in the hollow tube during a post-extrusion process. The hollow tube may include multiple lumens in a single tube, and the spring may be associated with one or more of the lumens. A G-J button may be coupled to the hollow tube at one end thereof. The multiple lumens may include a first gastric lumen, a second jejunal lumen, and a third lumen.

In another example, a kink-resistant tubing includes a tubing wall and a spring positioned one of inside the tubing wall or adjacent an interior surface of the tubing wall. The spring helps to deter the tubing from kinking when bent. When the spring is positioned inside the tubing wall, the spring is incorporated into the tubing wall during an extrusion manufacturing process of the tubing. When the spring is positioned adjacent the tubing wall, the spring is added to the tubing after the extrusion process has been completed.

In another example, a multi-lumen feeding tube that is coupled to a G-J button includes a multi-lumen and a spring positioned along at least part of the length of the multi-lumen tube. The multi-lumen tube has at least two lumens at a proximal end thereof and at least one lumen at a distal end thereof, with the lumens comprising at least a gastric lumen and a jejunal lumen. The spring is provided in order to provide a kink-resistant feature to the feeding tube.

The gastric and jejunal lumens are about the same length as one another and the multi-lumen feeding tubing also includes a jejunal tube inserted into the jejunal lumen, with the jejunal tube having a length that is greater than the length of the gastric and jejunal lumens. The spring is positioned along at least part of the length of the jejunal tube. The jejunal tube may have a cone-shaped portion at a proximal end thereof and the cone-shaped portion may be formed integrally with or formed in a post-processing step. The cone-shaped portion may be made of a higher durometer material than the material of the tube. The tube may be inserted into an opening in the G-J button into the jejunal lumen such that the cone-shaped portion seats in the G-J button to couple the jejunal tube to the jejunal lumen and G-J button.

The spring may be coupled to the jejunal lumen of the multi-lumen tube and the jejunal lumen may have a length that is greater than the gastric lumen, with the spring extending along at least part of the length of the jejunal lumen or along substantially all of the length of the jejunal lumen. The spring may be coextruded with the jejunal lumen such that the spring is embedded in the wall of the jejunal lumen.

The spring may be coupled to the outer wall of the multi-lumen tube such that the spring is co-extruded with the outer wall of the multi-lumen tube. The multi-lumen tube may have a substantially constant outer diameter along its length, and the multi-lumen tube may have at least a gastric lumen and a jejunal lumen, with the gastric lumen having a length that is less than a length of the jejunal lumen, and the spring extends along part or all of the length of the jejunal lumen.

BRIEF DESCRIPTION OF THE DRAWINGS

FIG. 5 is a plan view of tubing that is tri-lumen and transitions to bi-lumen;

FIG. 6 is a cross-sectional view of the tubing of FIG. 5 taken at line 6-6 of FIG. 5;

FIG. 7 is a cross-sectional view of the tubing of FIG. 5 taken at line 7-7 of FIG. 5;

FIG. 12 is a plan view of a first example G-J feeding tube;

FIG. 13 is a longitudinal cross-sectional view of the first example G-J feeding tube of FIG. 12 taken at line 13-13 in FIG. 12;

FIG. 14 is a plan view of a second example G-J feeding tube;

FIG. 15 is a longitudinal cross-sectional view of the second example G-J feeding tube of FIG. 14 taken at line 15-15 in FIG. 14;

FIG. 16 is an enlarged longitudinal cross-sectional view of the transition zone in FIG. 15, identified by the encircled area 16-16 in FIG. 15;

FIG. 17 is a plan view of a third example G-J feeding tube;

FIG. 18 is a longitudinal cross-sectional view of the third example G-J feeding tube of FIG. 17, taken at line 18-18 in FIG. 17;

FIG. 19 is an enlarged longitudinal cross-sectional view of the transition zone in FIG. 18, identified by the encircled area 19-19 in FIG. 18;

FIG. 20 is a longitudinal cross-sectional view of an example G-J feeding tube similar to that of FIG. 17;

FIG. 21 is a transverse cross-sectional view of the G-J feeding tube of FIG. 20, taken at line 21-21 of FIG. 20;

FIG. 22 is a transverse cross-sectional view of the G-J feeding tube of FIG. 20, taken at line 22-22 of FIG. 20;

FIG. 26 is a perspective view of the example feeding tube of FIG. 24;

FIG. 27 is a cross-sectional view of the example feeding tube of FIG. 26 taken at line 27-27;

FIG. 28 is a longitudinal cross-sectional view of the example feeding tube button portion of FIG. 27, taken at the encircled area 28-28;

FIG. 29 is a transverse cross-sectional view of the example feeding tube of FIGS. 23-24 and 26-28, taken at line 29 in FIG. 24;

FIG. 37 is an enlarged perspective view of a portion of the feeding tube of FIG. 34;

FIG. 38 is an enlarged plan view of a portion of the feeding tube of FIG. 34, taken at a different orientation than that shown in FIG. 37;

FIG. 39 is a transverse cross-sectional view of the example feeding tube shown in FIG. 38, taken at line 39-39; and FIG. 40 is a transverse cross-sectional view of the example feeding tube shown in FIG. 38, taken at line 40-40.

DETAILED DESCRIPTION

The examples described herein are directed toward tubing that utilizes a kink-resistant feature. This kink-resistant feature can be incorporated into G-J tubing, including single lumen or multi-lumen tubing or any other type of tubing. The kink-resistant tubing helps to maintain tubing patency and flow as the tube bends, twists and turns its way through the folds of the small intestine. While the tubing described herein is described in the context of G-J feeding tubes, it should be readily recognized that the examples described herein can be utilized in any type of system or application that requires non-kinking of tubing.

Figure 1:
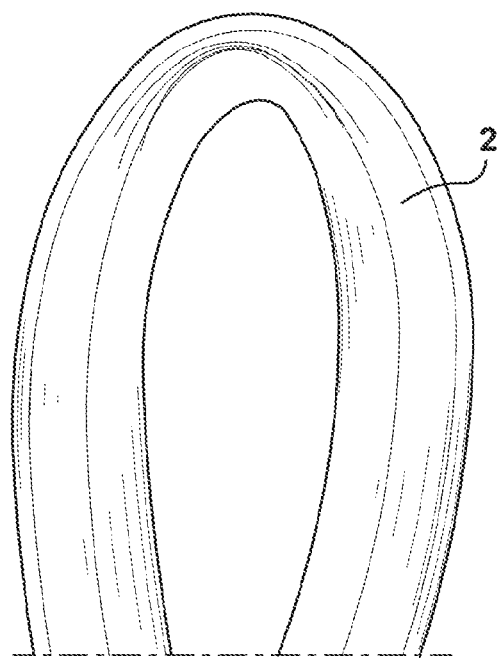
FIG. 1 is a plan view of a portion of a prior art kinked multi-lumen tube.
Figure 2:
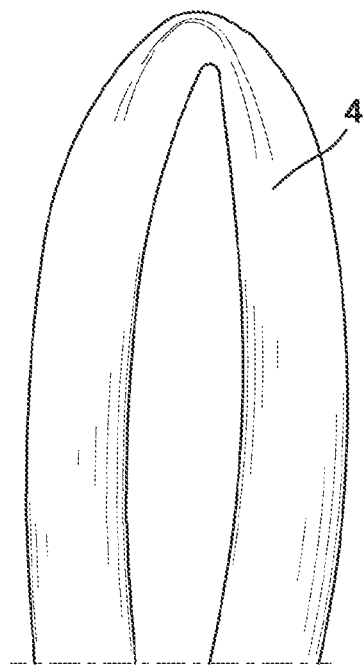
FIG. 2 is a plan view of a portion of a prior art kinked single lumen tube.
Figure 3:
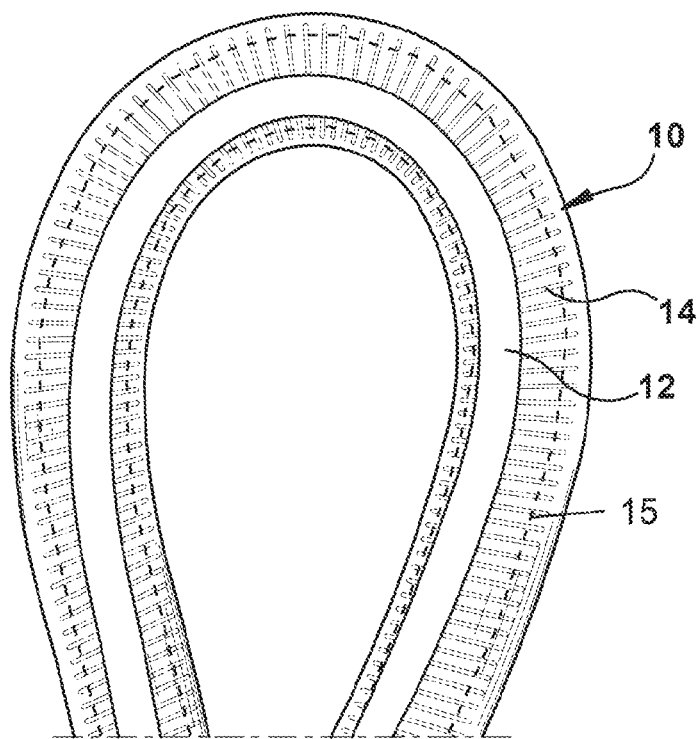
FIG. 3 is a plan view of a portion of an example kink-resistant tubing in a bent position.
Figure 4:
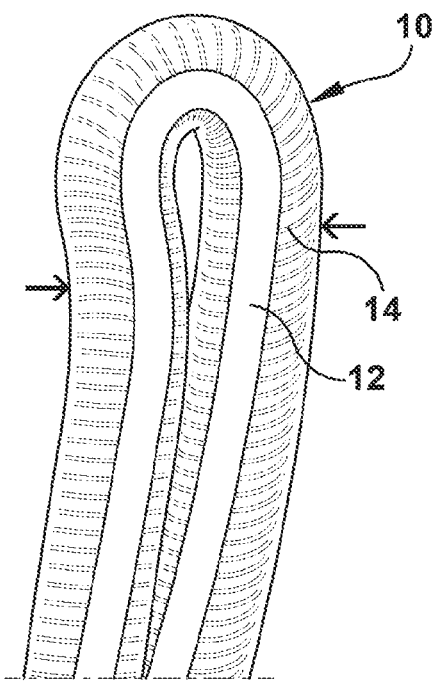
FIG. 4 is a plan view of a portion of an example kink-resistant tubing in a bent position.

In one example, shown in FIGS. 3 and 4, the kink-resistant tubing 10 is provided by utilizing a spring 14 that is adhered to the inner wall of the tubing. An encapsulant 15 may be used to adhere the spring 14 to the inner wall of the tubing 10. The tubing 10 may be silicone tubing and the spring 14 may be a stainless steel spring or a flexible polymeric spring, among other types of springs and tubings. By positioning the spring in the tube at an inner diameter of the tubing and encapsulating it, the outside diameter of the tubing 10 is not affected. This allows the tube 10 to maintain its soft, smooth silicone exterior. Other types of materials may be used for the tubing, such as other polymers including polyurethane. Thermoset or thermoplastic materials may be used for the tubing or for other parts of the system, as described in greater detail below.

The spring 14 may be positioned in the tubing and may be inserted into a round or somewhat round interior of tubing. The spring may be formed to fit within the interior shape of the tubing. Transitional tubing may not have an entirely round interior, but the spring 14 may still be used with transitional tubing. The spring is inserted into the interior of the tubing through the end of the tubing. Different size springs may be selected based upon the size (e.g., French size) and length of the tubing 10. The spring may traverse part of the length of the tubing, or all of the length of the tubing.

The spring 14 may be made of a biocompatible metal or of a flexible polymer. An example of a biocompatible metal is 316L stainless steel. Other metal and plastic materials may be used.

In the case of a post-extrusion secondary process for installing the spring 14 in the tubing 10, a support structure may be utilized for securely adhering the spring 14 to the inner diameter of the silicone tubing 10. The inside of the tubing 10 may serve as the support structure. Alternatively, a separate piece of tubing (not shown) may serve as the support structure. The separate piece of tubing that is used for the support structure should be sized so that it fits inside the inner diameter of the tubing 10. The support structure should allow the spring to be maintained on the interior of the tubing for at least 6-12 months. When the inner wall of the tubing is used as the support structure for the spring, the spring may be encapsulated against the support structure by an encapsulant. Because the tubing 10 is used in a lipid-rich environment, the spring 14, support structure, and encapsulant, if any, must be able to withstand the environment without corroding while maintaining tube flexibility. The tubing 10 should also be MRI-compatible, if desired. The spring 14, support structure, and encapsulant, if any, should produce a low profile within the tubing's inner diameter.

An example of kink-resistant tubing is depicted in FIGS. 3 and 4 for a multi-lumen tube that is used in G-J applications. In the examples shown, the spring is positioned in one of the lumens of the tubing, while one of the lumens remains free of a spring. Even when tightly pinched, as shown by the arrows in FIG. 4, the tubing 10 typically will not kink.

FIGS. 5-7 depict a multi-lumen tube 10 that incorporates a gastric lumen 16, a jejunal lumen 18 and a smaller third lumen 20. FIG. 6 depicts the proximal section of the tubing that utilizes three lumens and FIG. 7 depicts the distal section of the tubing that utilizes two lumens. The tubing shown in FIGS. 3-7 utilizes one or more stripes 12, 22 that are positioned on the outer wall of the tubing. The stripes may be utilized to identify the location of one of the lumen in the tubing. The stripes 12, 22 may be a barium-sulfate stripe that is radiopaque and that allows a physician to easily view the placement of the tubing 10 via x-rays. The spring 14 may also be radiopaque. In the tubing 10 shown, two stripes are used. One stripe 12 is wider than the other stripe and is positioned adjacent the large jejunal lumen of the multi-lumen tube 10. The narrower stripe 22 helps to locate the smaller gastric lumen 16 in the multi-lumen section of the tube. Typically, a G-J tubing 10 will have three lumens in the proximal (closest to the skin) section and two lumens in the distal section (the section that extends into the jejunum). The spring 14 may be maintained in one of the lumens, but keeps both lumens from kinking.

Figure 11:
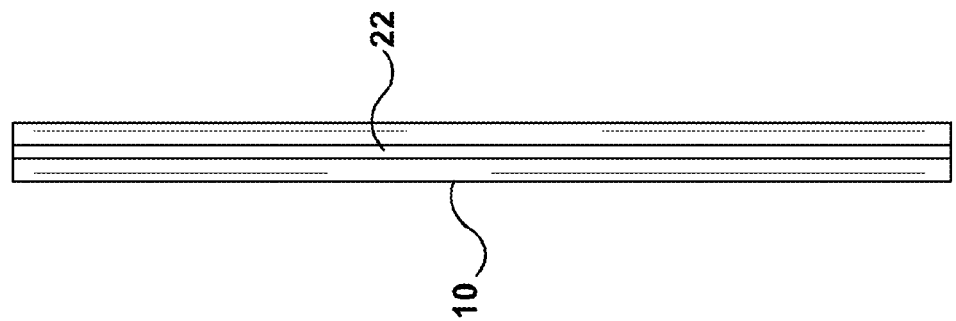
FIG. 11 is a side view of the tubing of FIG. 5 rotated 90 degrees about its axis relative to the view shown in FIG. 10.
Figure 10:
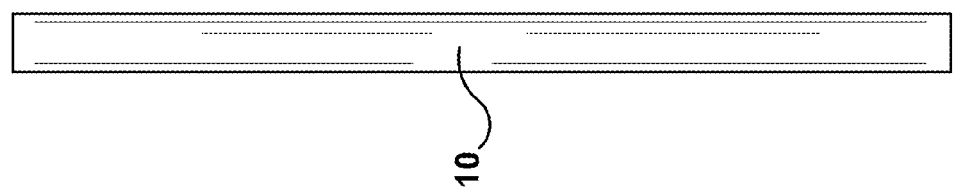
FIG. 10 is a side view of the tubing of FIG. 5 rotated 90 degrees about its axis relative to the view shown in FIG. 9.
Figure 9:
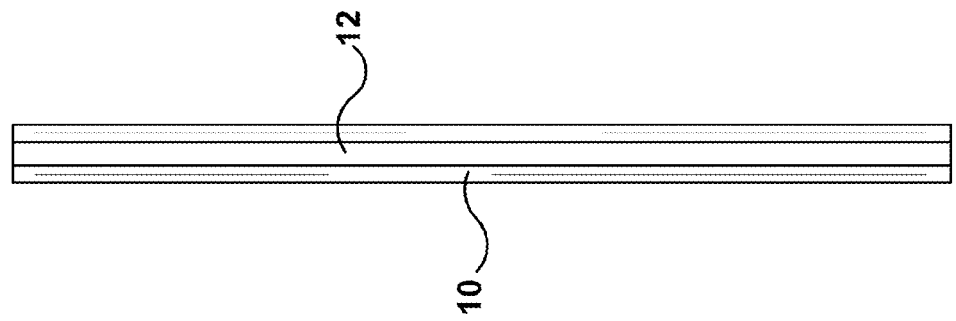
FIG. 9 is a side view of the tubing of FIG. 5 showing a strip on the tubing that is positioned adjacent the jejunal lumen of the tubing.
Figure 8:
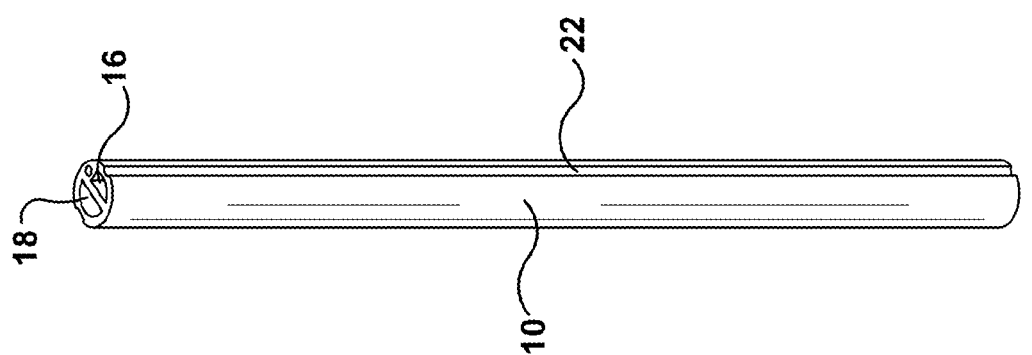
FIG. 8 is a perspective view of the tubing of FIG. 5.
Figure 25:
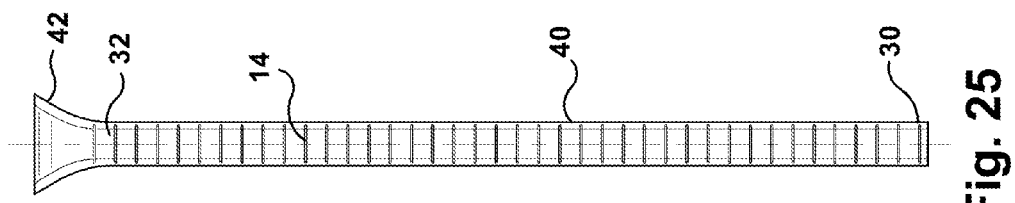
FIG. 25 is a plan view of the example kink-resistant tube that is incorporated into FIG. 24.
Figure 24:
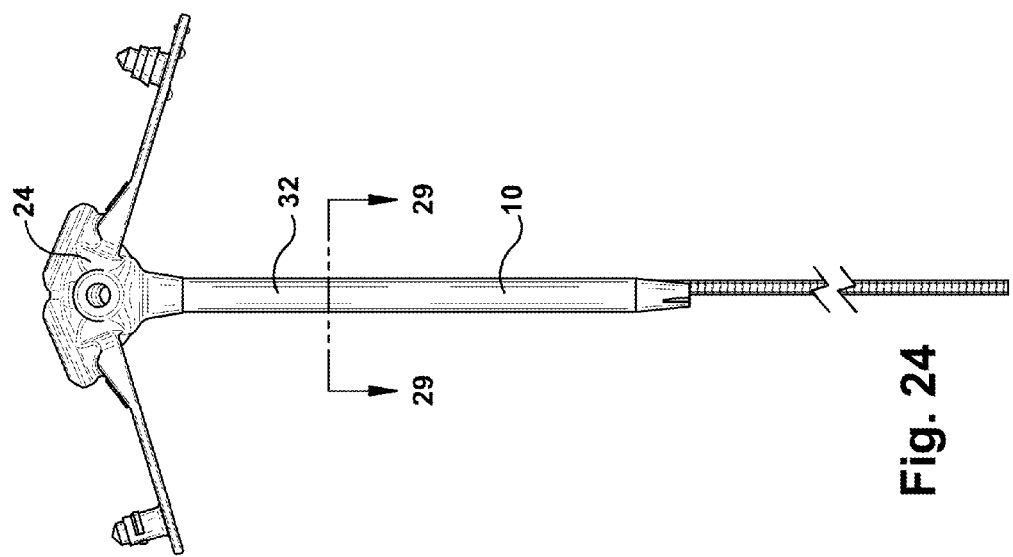
FIG. 24 is a perspective view of the triple lumen feeding tube of FIG. 23 incorporating an example kink-resistant tube.
Figure 23:
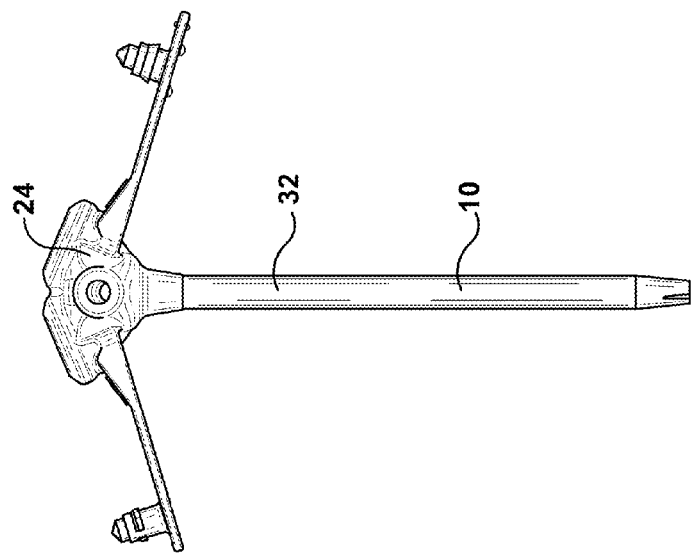
FIG. 23 is a perspective view of a triple lumen feeding tube.
Figure 33:
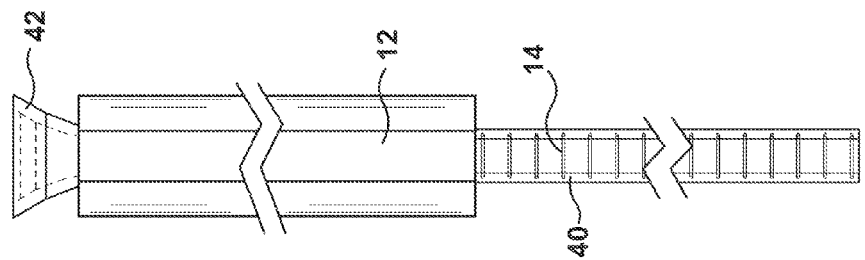
FIG. 33 is a plan view of the combined feeding tube and tri-lumen tubing of FIG. 30, oriented such that the jejunal lumen faces outwardly from the plane of the paper.
Figure 32:
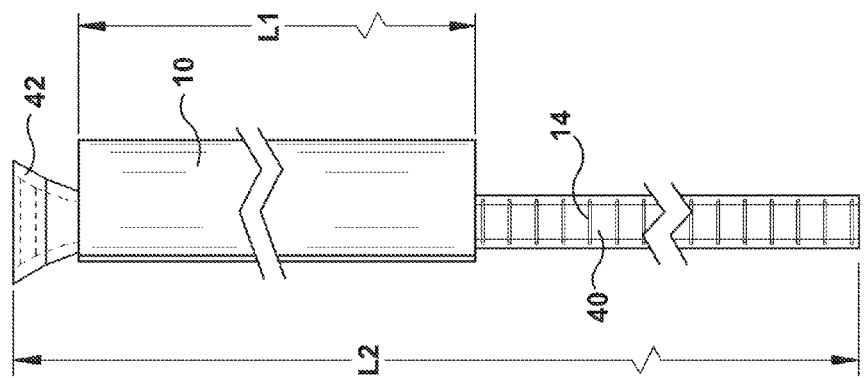
FIG. 32 is a plan view of the combined feeding tube and tri-lumen tubing of FIG. 30, oriented such that a side of tri-lumen tubing faces outwardly from the plane of the paper.
Figure 31:
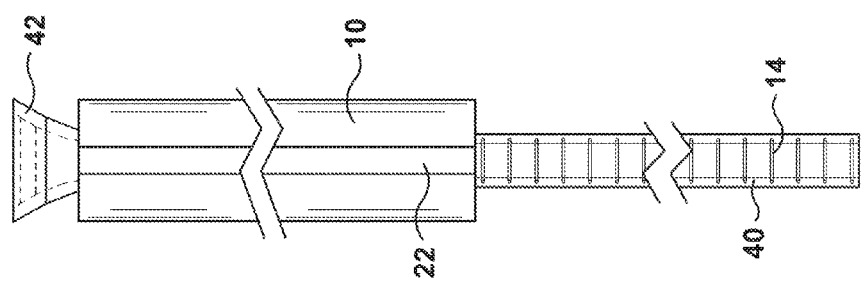
FIG. 31 is a plan view of the combined feeding tube and tri-lumen tubing of FIG. 30, oriented such that the gastric lumen faces outwardly from the plane of the paper.
Figure 30:
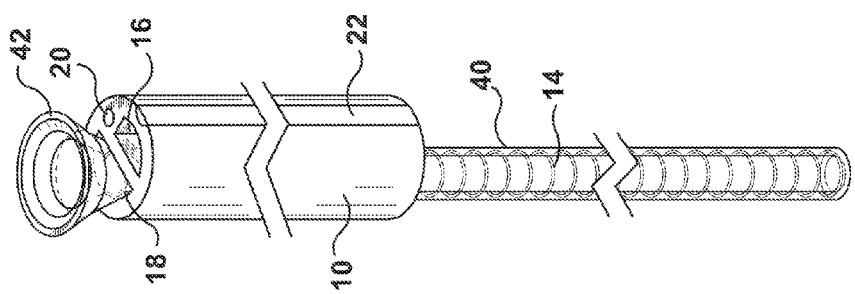
FIG. 30 is a perspective view of the example feeding tube of FIG. 26 inserted into a tri-lumen tubing.
Figure 34:
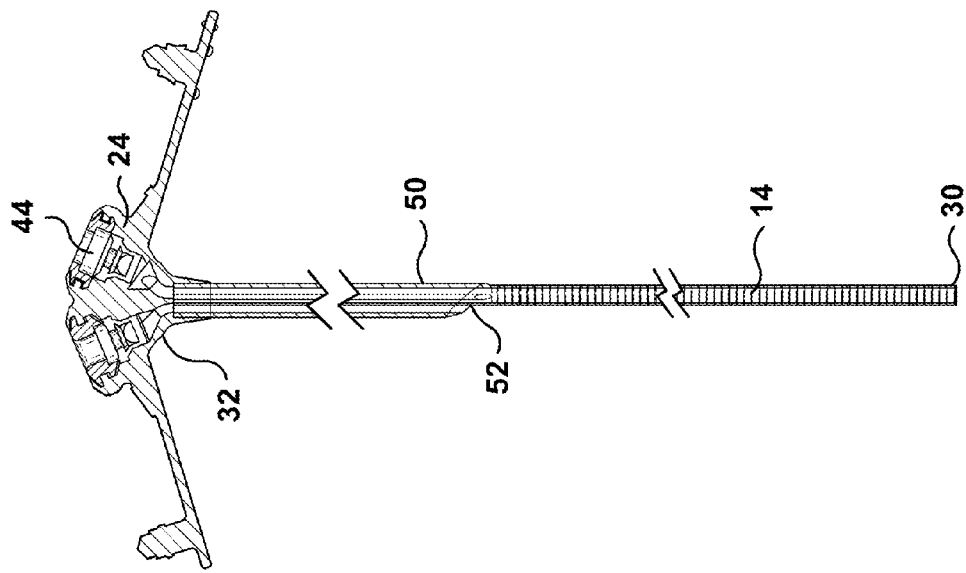
FIG. 34 is a perspective view of another example feeding tube.
Figure 35:
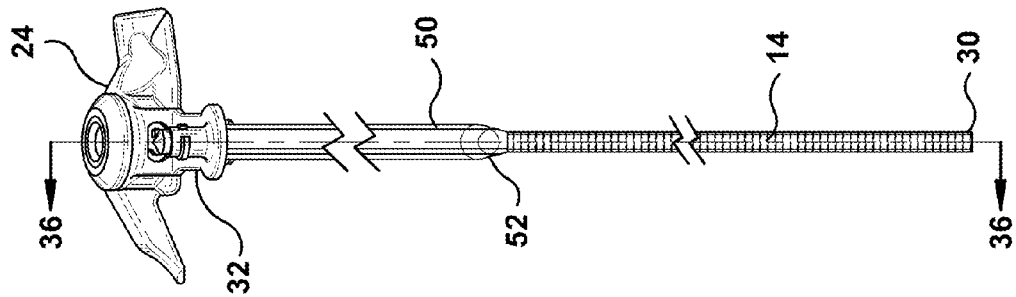
FIG. 35 is another perspective view of the example feeding tube of FIG. 34 taken at a different orientation.
Figure 36:
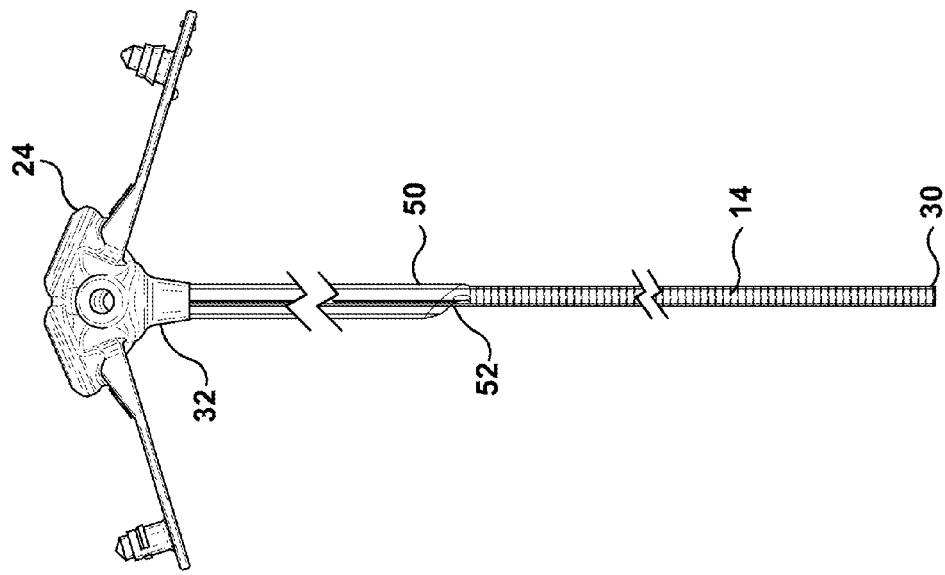
FIG. 36 is a longitudinal cross-sectional view of the example feeding tube of FIG. 35, taken at line 36-36.

FIGS. 8-11 depict the exterior of the tubing that utilizes the stripes 12, 22 to identify the position of the lumens. FIG. 8 depicts the tubing 10 with a narrow stripe 22 positioned along the gastric lumen 16. FIG. 9 depicts the tubing 10 with the wider stripe 12 positioned outwardly. The wider stripe 12 is positioned substantially in the middle of the jejunal lumen 18 on the exterior of the tubing 10. FIG. 10 depicts a portion of the tubing 10 that does not have stripes 12, 22. FIG. 11 depicts a narrower stripe 22, which is positioned adjacent the gastric lumen 16.

The following advantages are associated with the kink-resistant tubing:
1) Increased G-J Button longevity;
2) More reliable feedings for patients that already have difficulty receiving enough nutrition;
3) Reduces the number of G-J replacements by interventional radiology;
4) Reduces the number of hospital visits;
5) Reduces the patient's exposure to radiation;
6) Increases the possibility of developing even smaller G-J buttons than those used today, such as a 12 French button;
7) Provides peace-of-mind for parents, patients, and doctors;
8) Increases the possibility of preventing retrograde movement of the distal portion of the tubing 10 and preventing the tubing from coiling back into the stomach;
9) Improves the ability to use a medical-grade spring stainless steel, such as 316L stainless, that would show up very well during placement under fluoroscopy; and
10) Improves ability to maintain flow through the device even if the device begins to coil within the stomach.

Examples showing an example spring reinforcement positioned in the jejunal lumen at the transitional area of a G-J tubing 10 is shown in FIGS. 12-13. FIGS. 12 and 13 utilize a balloon 26 at the proximal end of the tubing. The tubing 10 is typically manufactured separate from the G-J button and the G-J button 24 is overmolded at the proximal end 32 of the multi-lumen tubing 10. The tubing 10 has three lumens, as described above in connection with FIGS. 5-7. The spring is positioned in the jejunal lumen beginning at the transition point 28 where the gastric lumen ends. As previously discussed, the gastric lumen ends and the jejunal and third lumens extend into the distal end of the tubing 10. In this example, a spring is positioned in the interior of the jejunal lumen after the transition point 28 and is encapsulated or extruded into the lumen, as discussed above. The G-J button may be any type of button utilized with G-J feeding. The distal end 30 of the tubing 10 may be rounded in order to provide easier travel through the intestines. As is evident, the spring 14 only extends along part of the length of the tubing 10. In one embodiment, the spring extends along about 6.5 inches of the length of the jejunal portion of the tubing.

FIGS. 14-16 depict another example embodiment of the tubing having a G-J button that is overmolded at the proximal end 32 of the tubing, similar to that shown in FIGS. 12 and 13. In this example, the spring is positioned in the jejunal section 18 of the tubing 10 and the transition between the jejunal lumen and spring and the proximal end of the tubing 10 is curved such that part of the spring 14 extends nearly to the tip 34 of the rounded portion. In this example, the spring 14 may be positioned inside the tubing after the tubing has been extruded or may be co-extruded with the jejunal lumen, but does not extend into the gastric lumen 16. As is evident, the spring 14 only extends along part of the length of the tubing 10. In one embodiment, the spring extends along about 6.5 inches of the length of the tubing.

FIG. 17-22 are similar to the examples shown in FIGS. 14-16, except the profile of the interior of the tubing in the transition zone 28 is squared instead of rounded. The spring 14 extends to the top 36 of the square portion in order to provide slightly better stability at the transition zone than the embodiment in FIGS. 14-16. As is evident, the spring 14 only extends along part of the length of the tubing 10. In one embodiment, the spring extends along about 6.5 inches of the length of the tubing. Other lengths for the spring may be utilized depending upon the application. The spring could extend along the entire length of the tubing, if desired. As with prior examples, the spring could be positioned inside the tubing after extrusion of the tubing (as shown in FIG. 22), or could be positioned in the tubing during the tubing extrusion process.

FIGS. 23-33 depict another example kink-resistant tubing for use with a multi-lumen feeding tube. In this example, the multi-lumen proximal portion of the tubing 10 is formed using an extrusion or other process. The G-J button 24 is overmolded over the tubing 10 at the proximal end 32 of the tubing. The system also includes a separately molded jejunal tube 40 that may optionally include a cone-shaped proximal portion 42. In this example, the separately molded jejunal tube 40 has the spring 14 coextruded with the tubing 40 during the tubing manufacturing process such that the spring is embedded into the wall of the tubing 40. The spring may extend from the proximal end 32 to the distal end 30 of the tubing 40. The cone-shaped portion 42 may be formed during the extrusion process, or may be overmolded onto the proximal end 32 of the tubing 40 in a post-processing step. The cone-shaped portion 42 can be a different material than the tubing 40 and may have a different durometer, such as a higher durometer. One reason for this is to provide a slightly stiffer cone-shaped portion 42 so that the cone-shaped portion 42 can more readily mate with an interior surface of the G-J button 24.

FIGS. 26-29 show how the jejunal tube 40 is positioned inside an existing multi-lumen feeding tube 10 and G-J button 24. The jejunal tubular portion 40 is inserted into the jejunal opening 44 of the G-J button 24 and pressed into the jejunal opening 44 until the cone-shaped portion 42 of the tube 40 seats into a similarly shaped cone-shaped portion 46 inside the jejunal opening 44 of the button 24. Isopropyl alcohol can be used as a lubricant in order to insert the jejunal tube 40 into the jejunal lumen 18. The cone-shaped portion 42 of the tube 40 may bite into the material of the G-J button 24 until it seats inside the cone-shaped opening 46 and fits in the cone-shaped opening so that no space is provided around the cone-shaped portion 42 inside the jejunal opening 44. The tight fit between the cone-shaped portion 42 and the cone-shaped portion 46 of the button 24 ensures that there is little or no leakage around the cone-shaped portion 42. The cone-shaped portion's 42 tight fit helps to hold the tube 40 in position inside the multi-lumen tubing 10. This example permits a kink-resistant tubing 40 to be utilized with existing multi-lumen tubes 10 and G-J buttons 24. As shown, the spring 14 extends along the full length of the tube 40. Alternatively, the spring 14 could be positioned to extend along only part of the tube 40, if desired. If necessary, an adhesive, such as a silicone adhesive, may be used to adhere the jejunal tube 40 inside the jejunal lumen 18. An adhesive may also be used to secure the cone-shaped portion 42 inside the cone shaped portion 46 of the button. Other adhesives may be used. While the jejunal tube 40 is shown as having a cone-shaped portion 42, the cone-shaped portion is optional. Moreover, the cone-shaped portion may include a spring 14 or may not include a spring, if desired. The cone shaped portion 42 may be overmolded onto the tubing or may be integrally molded with the tubing.

FIGS. 30-33 show how the tube 40 is positioned inside the jejunal lumen 18 of the multi-lumen tube 10 and how the tube 40 extends out of the bottom of the multi-lumen tube 10. In this example, the jejunal lumen is provided by the tube 40, instead of a separately added jejunal lumen. FIGS. 30-33 also show how the cone-shaped portion abuts against the top of the multi-lumen portion of the tubing 10. Typically, as described above, the tube 40 and cone 42 are inserted into the G-J button opening 44, so the examples shown in FIGS. 30-33 are for illustration purposes only to show general placement and orientation of the tube 40 relative to tube 10. The stripes 12, 22 that represent the positions of the gastric and jejunal lumens are also shown. The length L1 of the multi-lumen portion may be about 3 inches while the length L2 of the entire device from the top of the multi-lumen portion to the distal end of the tubing 40 may be about 23 inches. Other lengths may be employed. In addition, it is possible for the tube 40 to be cut to length, if desired.

FIGS. 34-40 depict another example kink-resistant tubing embodiment. In this example, the multi-lumen tubing 50 is coextruded with the spring 14 such that the spring 14 is positioned inside the multi-lumen portion 50 of the tubing and extends out from the base 52 of the multi-lumen tubing 50 to provide the jejunal lumen 18. As with the prior examples, the G-J button 24 may be overmolded over the multi-lumen tubing 50 after the multi-lumen tubing is formed using an extrusion process. This example provides for flexibility in sizing the openings of the gastric lumen 16 and jejunal lumen 18. In addition, it permits the entire length of the feeding tube to incorporate a spring in order to provide a kink-resistant feature. After the jejunal lumen 18 transitions from the multi-lumen portion 50 of the feeding tube, the spring remains embedded in the wall of the jejunal lumen 18.

Another example of a kink-resistant tubing embodiment is described. In this example, the spring 14 is positioned in an outer wall of the multi-lumen portion and the diameter of the multi-lumen portion remains substantially the same along the entire length of the feeding tube. As with prior examples, the G-J button 24 may be overmolded over the proximal end of the feeding tube. Stripes 12, 22 may be positioned on an exterior surface of the feeding tube. The spring 14 is embedded into the outer wall of the feeding tube. When the feeding tube transitions from tri-lumen to bi-lumen, the outer diameter of the tube remains the same. This example allows for a thin outer wall of the feeding tube because the spring 14 provides reinforcement of the wall of the feeding tube. Thus, with this embodiment, it is possible to have a smaller diameter feeding tube because greater area inside the feeding tube can be used to provide the lumens. In this example, the tri-lumen portion of the tubing may have a length L3 of about 4 inches, the bi-lumen portion may have a length L4 of about 19 inches, and the total length L5 for the feeding tube may be about 23 inches. Other lengths may alternatively be used.

As previously discussed, the spring may be inserted into the tubing during the tubing extrusion process as an alternative to a post-extrusion insertion process. The tubing may be silicone, polyurethane, or other types of materials.

The use of a polymeric spring instead of a metal spring allows for the device to be considered MRI "safe". Polymeric coils may be more easily cut by a physician to a specific length. This would also make it less likely for there to be a sharp end at the place where the tubing is cut since no metal is utilized.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A multi-lumen feeding tube device comprising:
   a multi-lumen tube having at least two lumens at a proximal end thereof and at least one lumen at a distal end thereof, with the at least two lumens comprising at least a gastric lumen and a jejunal lumen;
   a G-J button;

a jejunal tube inserted into the jejunal lumen, wherein the jejunal tube comprises a cone-shaped portion at a proximal-most end of the jejunal tube that expands radially from the jejunal tube, and the jejunal tube is inserted into an opening in the G-J button into the jejunal lumen such that the cone-shaped portion mates with an interior surface of the G-J button to couple the jejunal tube to the jejunal lumen and the G-J button; and a spring positioned continuously along a length of the jejunal tube from just below the cone-shaped portion at the proximal-most end in order to provide a kink-resistant feature to the multi-lumen feeding tube device.

2. The multi-lumen feeding tube device of claim 1, wherein the gastric lumen and the jejunal lumen are about the same length within a length of a tri-lumen portion with the jejunal tube having a length that is greater than the length of the gastric lumen and the jejunal lumen.

3. The multi-lumen feeding tube device of claim 1, wherein the cone-shaped portion is formed integrally with the jejunal tube or in a post-processing step.

4. The multi-lumen feeding tube device of claim 1, wherein the cone-shaped portion is made of a higher durometer material than the rest of the jejunal tube.

5. The multi-lumen feeding tube device of claim 1, wherein the spring is embedded into a wall of the jejunal tube.

6. The multi-lumen feeding tube device of claim 1, wherein the spring is inserted into the jejunal tube and is in contact with an inner wall of the jejunal tube.

7. The multi-lumen feeding tube device of claim 1, wherein the multi-lumen feeding tube device further comprises a barium-sulfate stripe positioned on an outer wall of the multi-lumen tube.

8. The multi-lumen feeding tube device of claim 1, wherein the spring is radiopaque.

9. The multi-lumen feeding tube device of claim 1, wherein the spring comprises a Magnetic Resonance Imaging-safe polymeric spring.

10. The multi-lumen feeding tube device of claim 1, wherein the cone-shaped portion comprises another spring.

11. The multi-lumen feeding tube device of claim 1, wherein the interior surface of the G-J button with which the cone-shaped portion mates is a distal interior surface of the G-J button.

* * * * *